United States Patent [19]

Lustig

[11] Patent Number: 4,689,013

[45] Date of Patent: Aug. 25, 1987

[54] MODULAR SYSTEM FOR RESTORATIVE DENTISTRY

[76] Inventor: Leopold P. Lustig, 304 Greenwood St., Newton Centre, Mass. 02159

[21] Appl. No.: 839,218

[22] Filed: Mar. 13, 1986

Related U.S. Application Data

[63] Continuation of Ser. No. 685,138, Dec. 17, 1984, abandoned.

[51] Int. Cl.⁴ ............................................. A61C 13/12
[52] U.S. Cl. ..................................... 433/181; 433/180; 433/183; 433/192; 433/213
[58] Field of Search ............... 433/180, 181, 182, 183, 433/177, 191, 192, 193, 213, 171, 190

[56] References Cited

U.S. PATENT DOCUMENTS

| | | | |
|---|---|---|---|
| 1,211,494 | 1/1917 | Shaw | 433/181 |
| 1,262,705 | 4/1918 | Shaw | 433/193 |
| 1,671,781 | 5/1928 | Phillips | 433/183 |
| 2,194,790 | 3/1940 | Gluck | 433/183 |
| 2,213,964 | 9/1940 | Myerson | 433/183 |
| 2,279,351 | 4/1942 | Skinner | 433/190 |
| 2,826,814 | 3/1958 | Sappey et al. | 433/193 |
| 3,344,842 | 10/1967 | Cameron | 433/181 |
| 3,423,827 | 1/1969 | Bahm et al. | 433/183 |
| 3,641,670 | 2/1972 | Karageorge | 433/180 |
| 4,272,241 | 6/1981 | Crisalli | 433/171 |

FOREIGN PATENT DOCUMENTS

| | | | |
|---|---|---|---|
| 3008014 | 9/1981 | Fed. Rep. of Germany | 433/167 |
| 276547 | 10/1951 | Switzerland | 433/190 |

Primary Examiner—John J. Wilson

[57] ABSTRACT

A system of modular components for making dental restorative bridges, and a new method of making dental restorative bridges, using bars and fittings for fixing them between abutments, and prefabricated modules which provided pontic incisal and occlusal portions in a wide variety of shapes, shades, sizes and constructions. These modules are on substructures which are precision fitted to the bars. The soft-tissue oriented portion of each pontic is affixed to the gingival aspects of the bar and the module, after occlusal adjustment of the module has been made.

9 Claims, 27 Drawing Figures

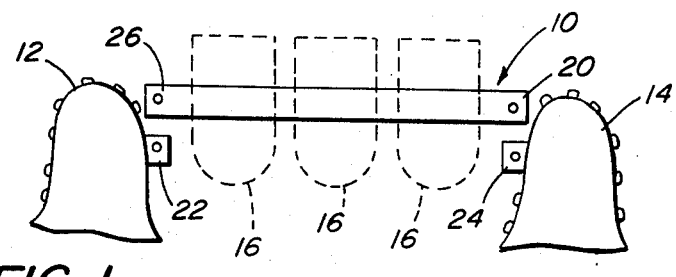
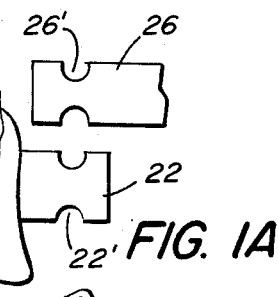
FIG. 1     FIG. 1A
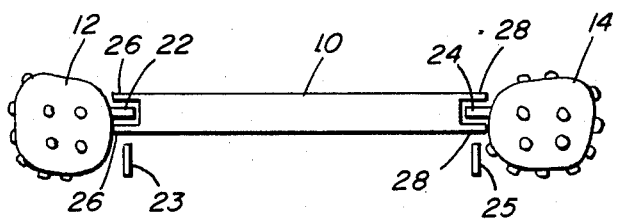
FIG. 2     FIG. 1B
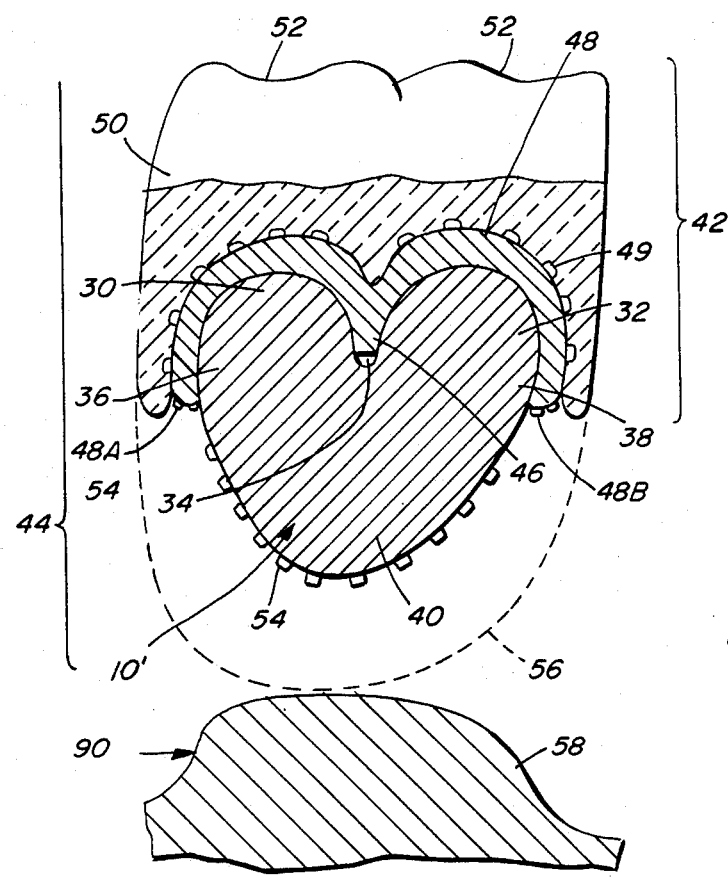
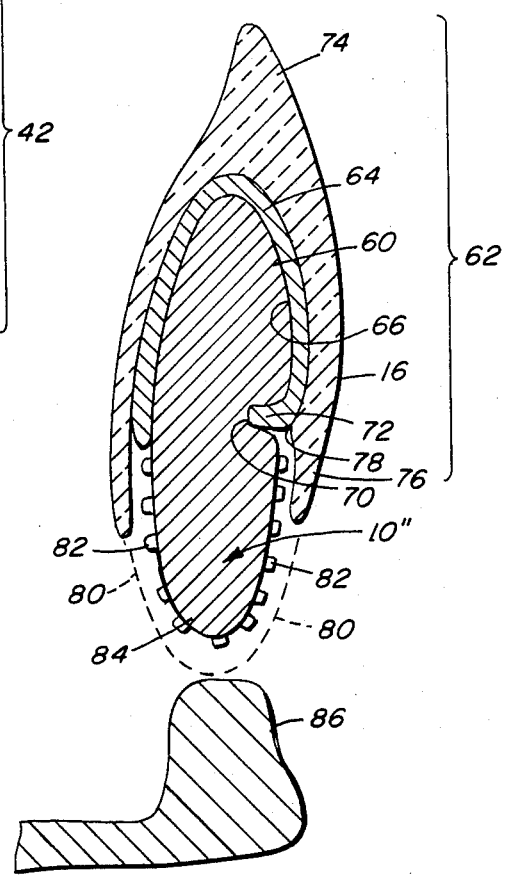
FIG. 3     FIG. 4

MODULAR SYSTEM FOR RESTORATIVE DENTISTRY

This application is a continuation of application Ser. No. 685,138 filed Dec. 17, 1984, now abandoned.

BACKGROUND OF THE INVENTION

This invention relates to dental restorative bridgework, more particularily to a modular system for restorative dentistry which makes possible the provision of permanently installed replacement teeth which can be shaped to an individual patient's needs by modification of pre-fabricated parts at a relatively low cost and in a relatively short time, in contrast to fixed bridgework that is made entirely in an outside laboratory from impressions taken on the patient.

Prior attempts to provide a series of component parts to be assembled into a dental bridge from a commercial package of parts have yielded only fixed bars or beams on which removable pontics are carried. These pontic devices use clamps, springs, and the like, which are subject to wear and breakage due in part to undesirable stress concentrations, and do not provide the accuracy of fit that can be provided by permanently fixed artificial teeth. They generally lack complete lower portions, and so are cosmetically unsightly, and tend to be unsanitary and therefore not bio-compatible.

The fabrication of fixed bridgework entirely in an outside laboratory from impressions taken on the patient is expensive and time consuming. In the present state of the art, a dentist has a choice between ceramo-metal bridgework, and bridgework made out of cast gold (or other precious or semi-precious metal) with acrylic facings. Both techniques are technologically complex and require people with special skills. In practice it is found to be unrealistic to expect that a dental technician, who in the vast majority of cases is located at a considerable distance from the dentist and patient will be able to produce the bridgework with the required accuracy of fit and occlusion and the desired cosmetic appearance. It is not unusual for a dentist in search of a competent laboratory to send work to one located hundreds or thousands of miles away. Even then, critical occlusal adjustments are most often required after the finished bridgework has been permanently installed in the patient's mouth. Not unexpectedly, the cost of this form of restorative dentistry has escalated dramatically.

The present invention has as principal objects to minimize the use of outside skills and to give the dentist replacement tooth modules or elements (pontics) which will enable the dentist to provide fixed bridges from prefabricated component parts which will fit as accurately as and are cosmetically equal or superior to custom-made permanent bridgework and which can be made in shorter time and at less cost than custom-made permanent bridgework. The invention contemplates the provision of a wide variety of component parts, including pontics in a wide variety of sizes, shapes, and shades, which can be ordered by the dentist for early delivery from a central depot, to replenish the dentist's own stock as needed. The invention further contemplates unique methods and means to make occlusal adjustments, and to fabricate complete pontics in the patient's mouth, to the end that high quality restorative dentistry will be available at greatly reduced cost to a larger number of consumers.

THE PRIOR ART

U S. Pat. No. 1,118,703-Todd-shows a bridge consisting of a plurality of teeth fastened together between two terminal crowns; each tooth has, as separate parts, a base and a cap which are mechanically attached and then cemented together, the bases being saddle-shaped "so that they may bear firmly on the gums". The caps are metallic, and may be soldered together, or cast or molded as an integral structure (page 1, lines 101-115). 1,262,705 -Shaw-shows a bar permanently fixed at its ends to two teeth between which a tooth has been removed, and a U-shaped artificial tooth, or "dummy", removably fitted astride the bar. U.S. Pat. No. 1,211,494 -Shaw-shows an adjustable-length bar permanently fixed between two teeth abutting an open space; the artificial teeth, or pontics, carried by this bar are not described or identified. U.S. Pat. No. 1,465,473 -Hansen-shows a removable anterior tooth, an entire backing for which is fixed between two terminal crowns. U.S. Pat. No. 1,761,312 -Richardson-shows attachments bolted to a pontic. U.S. Pat. No. 2,826,814 -Sappey et al shows a bar permanently fixed between two abutment teeth, and a U-shaped removable pontic element carried by the bar.

The removable pontics, or artificial teeth, of Shaw and Sappey et al are designed to be put on and taken off the supporting bridge or bar by the user, with a motion that is transverse to the length of the bar, which has a generally rectangular cross-section.

GENERAL NATURE OF THE INVENTION

The present invention provides a substantially flexure-resistant beam of rounded cross-section as a carrying bar for a pontic, the beam incorporating means to support in fixed retention, against both the compressive forces of occlusion and any contact-derived forces of displacement around the beam, a pontic incisal or occlusal portion having occlusal and/or incisal contact surfaces with adjacent buccal and/or labial surfaces, and further means to retain a locally-applied dental reconstruction material for completing the soft-tissue oriented portion of the pontic after the incisal or occlusal pontic portion has been fixed in place. For convenience in this specification, and the appended claims, the pontic incisal or occlusal portion will be referred to as the "upper portion", and the soft-tissue oriented portion of the pontic will be referred to as the "lower portion". The compressive forces of occlusion on the pontic upper portion are distributed over the surfaces of the beam to minimize stress concentration in the pontic. The beam has two end supports which can take any of a wide variety of forms. The beam, its supports, and pontic upper portions can be prefabricated and made available to dentists commercially in a kit or package form, for assemblage into a fixed bridge fitted to an individual patient. The pontic upper portions can be provided in a wide variety of shapes, shades, sizes and constructions, to suit the needs and desires of patients, as well as the techniques preferred by individual dentists.

The soft tissue-oriented surfaces (gingival aspects) of both the beam or bar and the prefabricated upper portion have retentive means to provide fixation to the lower portion, which latter is fashioned-individually-at chair-side or on the master cast, out of plastic, composite or other soft material which can be hardened after being shaped, as by a catalyst, light-curing or other means. After the lower portion is cured, it contributes to rigidity of the bar and fixation of the pontic. The pontic upper portions have interdigital lobate shapes which include retentive projections that coincide with developmental patterns of natural dentition; the soft material will flow into the lobate shapes, thereby blending with the upper portion of the cosmetic pontic material, contributing to strength, without exhibiting a junction line.

BRIEF DESCRIPTION OF THE DRAWINGS

FIG. 1 illustrates the general nature of the invention;

FIGS. 1A and 1B show variation of attachment structures;

FIG. 2 is a top view of FIG. 1;

FIG. 3 is an enlarged cross-sectional view of the invention as applied to posterior teeth;

FIG. 4 is an enlarged cross-sectional view of the invention as applied to anterior teeth;

DETAILED DESCRIPTION OF THE DRAWINGS

Figure 5:
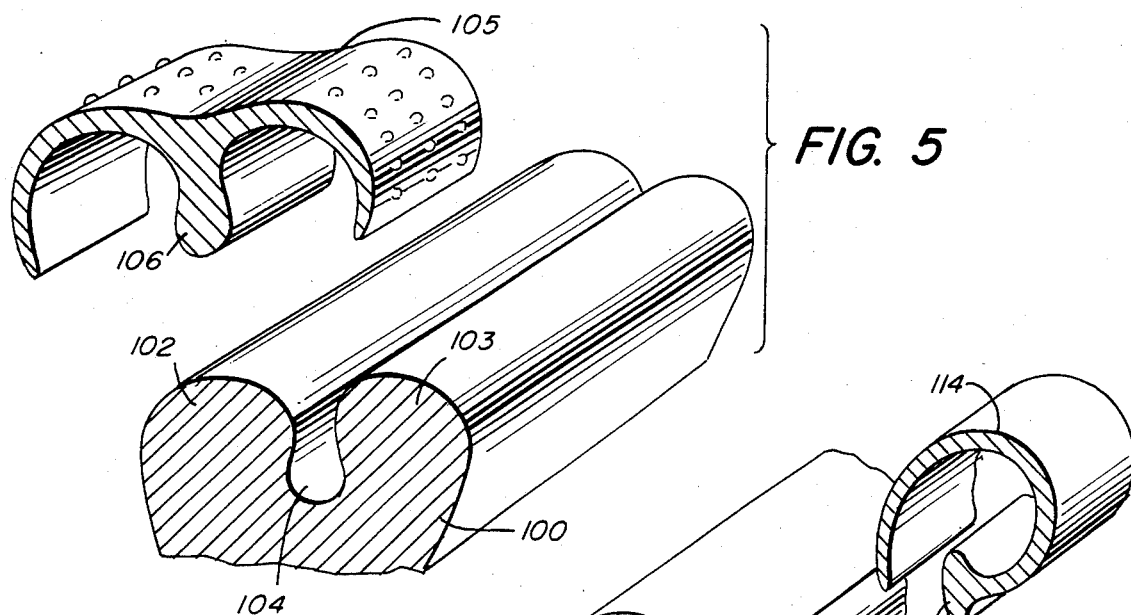
FIG. 5 is a partial view showing a modification of FIG. 3.

FIGS. 1 and 2 illustrate one way to fix in place a restoration using the invention. A beam 10 is pivotally connected at each end to a pair of copings 12, 14, which are intended to fit over prepared teeth, implants, posts or other structures or preparations (not shown) between which one or more pontics 16 (shown in dashed line on the bar in FIG. 1) are to be fitted. Each coping has a stud 22, 24, respectively, bored to receive a pivot pin 23, 25, respectively. Each end of the beam is bifurcated, providing two legs 26 at one end for embracing the first stud 22, and two legs 28 at the other end for embracing the second stud 24. Holes are provided in the studs and legs to receive the pins, 23 in stud 22 and legs 26, and 25 in stud 24 and legs 28, respectively. Alternatively, the hinge bifurations can be placed on the copings, and the studs at the ends of the beam.

To enhance rigidity of fixation and rigidity between the beam and each coping, multiple holes, such as pairs of notches 22' and 26' with a ligature wire 23' (FIG. 1A), or pairs of holes 22" and 26" with a U-shaped bolt 23" (FIG. 1B) can be used, for example, at one or both ends of the beam. In the latter case (FIG. 1B) the ends of the U-shaped bolt 23" can be bent over the end 26 of the beam after installation.

The beam 10 is a flexure-resistant beam of generally rounded cross-section, examples of which are illustrated in FIGS. 3, 4, 12 and 15. FIG. 3 shows a form suited for supporting molars and bicuspids; i.e.: posterior teeth. FIG. 4 shows a form suitable for supporting anterior teeth, an incisor being illustrated.

Referring to FIG. 3, the beam 10' has a generally heart-shaped cross-section. As viewed in the figure, two upwardly-facing (i.e.: occlusally-facing) lobes 30, 32 have a valley or groove 34 between them. The lower sidewalls 36, 38, of the lobes 30, 32, respectively, converge toward the bottom 40 of the heart-shaped cross-section. The upper part 42 of a pontic 44 rests on the lobes 30, 32, being retained against displacement around of the beam 10' by means of a spline 46 fitting into the valley 34 between the lobes.

The pontic upper part 42 is made in two parts, a substructure 48 which embraces the two lobes 30, 32 and provides the spline 46, and a superstructure 50 which includes the occlusal contact surfaces 52. The substructure may be made of any suitable metal or plastics material; it includes edge portions 48A and 48B which if made of a flexible material (e.g.: plastic) may extend to the lower sidewalls 36, 38, respectively, of the lobes 30, 32. If the substructure 48 and the superstructure 50 are joined in the factory, the substructure will be rigid, and cannot extend beyond the widest portion of the beam or bar. Together with the spline 46, the edge portions 48A and B of the substructure intimately embrace the upper part of the beam 10'. The substructure 48 has lower surfaces contoured so that they will closely match the confronting upper surfaces of the lobes 30, 32, so that forces arising from occlusal pressure on the contact surfaces 52 will be uniformly distributed from the pontic upper part 42 to the beam 10', and the opportunity for creation of sharp stress at any point in the pontic will be minimized. This feature is in marked contrast to the structure of Sappey et al., for example, where the rectangular edges of the bar (18) will concentrate stresses in the inside rectangular edges of the slot (21) in the pontic (19).

The pontic upper part 42 can be furnished as a prefabricated tooth part the substructure 48 of which is dimensionally matched to a bar or beam 10', thus assuring a precision fit between the substructure 48 and the lobes 30, 32 and valley 34. The substructure 48 has retentive means such as beads or scales 49 for retaining the superstructure 50. Pontic upper parts 42 can be furnished in sets offering a multitude of contours, shades and sizes of molar and bicuspid superstructures 50 among which to choose replacement teeth which will most nearly suit the needs of a particular patient.

The dentist can complete the prothesis at the patient's chairside. The substructure 48 and superstructure 50 can be fastened together in manufacture, or they can be supplied separately. In either case, the pontic upper part 42 will be fixed to the beam 10' by the dentist using fastening means and materials that are available to dentists. During this procedure the dentist will make necessary occlusal adjustments. This is a marked advantage over bridge work made in an outside laboratory from the patient's impressions, where final occlusal adjustments must often be made after all the expenses of fabricating and installing the bridges have been incurred.

Superstructures 50 can be made of a wide variety of materials. They can be supplied cured; or in a plastic state, to be formed in the patient's mouth by biting with opposing teeth to adjust to the proper occlusal height, after which they can be cured by light polymerization, or other catalyzing processes.

The gingival aspect of the beam 10' as seen in cross-section in FIG. 3, namely, part 40 of the cross-section, has on its outer surface retention means such as projections 54, sometimes called retentive beads, or scales, or other effective means of retention, for retaining a dental cosmetic material; e.g.: acrylics, ceramics or composite materials. The dentist will fashion the lower part 56 of each pontic by individualized fittings of each replacement element at chairside. This will be done by adding a dental restorative preferably layer-by-layer, in order to achieve complete hardening or setting of the material, and to fill the crevasses between the beam-substructure margin, and the lower edges of the super structure 50. subsequently, additional soft restorative material will be added to the soft-tissue aspect of the hardened restorative, orienting it toward the soft tissue so as to produce a tissue imprint on the tissue side of the pontic, and shaping it properly and removing the excess restorative material, prior to curing the additional material, once the desired shape is achieved. The restorative material will be hardened by whatever means are indicated for it. After all the restorative material has been applied to the pontics and to the abutment copings 12, 14, then the final contouring, staining and glazing will be done, and the bridge will be cemented in permanently.

Thus, the invention provides methods and means to fit individual artificial teeth from a stock of manufactured parts without the expense and delays of taking impressions and making castings in a laboratory, and with occlusal adjustments made at chairside, early in the fabrication procedure. Only the copings 12, 14 with their retentive means, e.g.: beads, will necessarily have been individually made earlier in a laboratory.

Referring to FIG. 4, the bar or beam 10" for anterior teeth will preferably have a thinner cross-section than the beam 10' for posterior teeth. A generally oval cross-section, with a longer cross-sectional dimension oriented vertically, is shown. As viewed in the figure, the upper part 60 of the beam cross-section is rounded somewhat like one of the lobes 30 or 32 in FIG. 3. An upper pontic part 62 has a substructure 64 which embraces the upper part 60, coming down over the front surface 66. Running longitudinally in the front surface 66 of the beam is a groove 70, and the substructure ends in a bent-inward front edge 72 which engages tightly in this groove. The superstructure 74 of the upper pontic part 62 is shaped as an incisor, and is made of a suitable cosmetic dental material. The front portion 76 of the superstructure depends below the front edge 78 of the substructure, and ends in a lobular configuration (illustrated in FIG. 9) which will enable cosmetic material for completing the lower pontic part to be blended without showing a visible line between the upper and lower parts.

As in the case of posterior teeth, the anterior tooth will be completed by applying cosmetic tooth restorative material 80 to retentive means (e.g.: beads or scales 82) on the surface 84 of the ginival aspect of the beam 10". The pontic will be completed as close to the gum 86 as the dentist chooses to do it.

Figure 6:
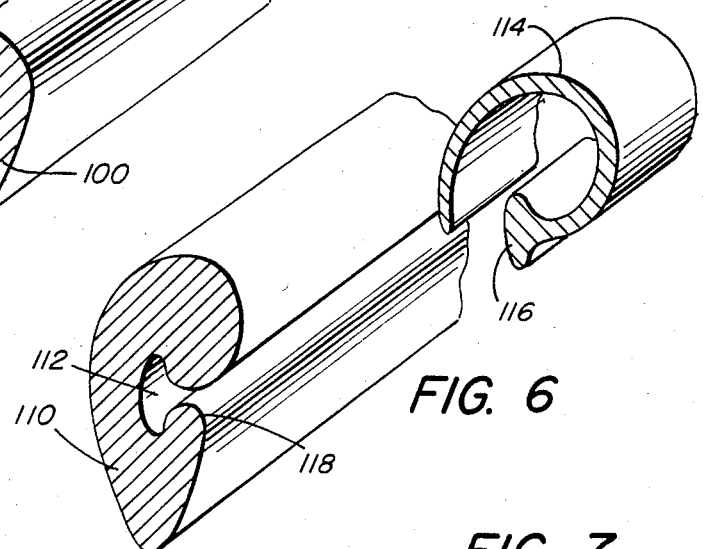
FIG. 6 is a partial view showing a modification of FIG. 4.

A pontic upper portion as shown in FIGS. 3 and 4 can be fitted to a beam by bringing its substructure to the beam from a side, or by sliding the substructure onto the beam from one end. FIGS. 5 and 6 illustrate beams 100 and 110 which are designed for sliding a pontic upper part onto the beam from one end.

In FIG. 5, which is a variant of the beam shown in FIG. 3, the valley 104 between the lobes 102, 103 is wider at the bottom than further up between the lobes, being shaped as a keyway. A mating substructure 105 of a pontic upper part (not shown) has a key 106 which can be fitted into the keyway 104 by sliding the substructure 105 onto the beam 100 from one end.

In FIG. 6, which is a variant of the beam shown in FIG. 4, the longitudinal groove 112 in the facial aspect 118 of the beam 110 is shaped as a dovetail, and in the mating substructure 114 for an anterior pontic the front edge is shaped as a key 116 matching the dovetail 112. The substructure 114 is fitted onto the beam 110 by sliding the substructure onto the beam from one end, with the key 116 in the dovetail groove.

The invention can be practiced with beams or bars that are free at each end, or that are hinged or attached at one end to an abutment, or to a coping 12 or 14. Thus, one of the pins 23, 25 can be put in place to function as a hinge-pin, if desired. The same principles can be applied without copings by affixing beams or attachments via a structure adapted to relatively intact abutment teeth, and subsequently bonding with adhesives to those teeth, thus providing tooth replacement by non-envasive means. Other forms of hinges, attachments and the like can be used. Some are described below with reference to FIGS. 20–25, inclusive.

Figure 7:
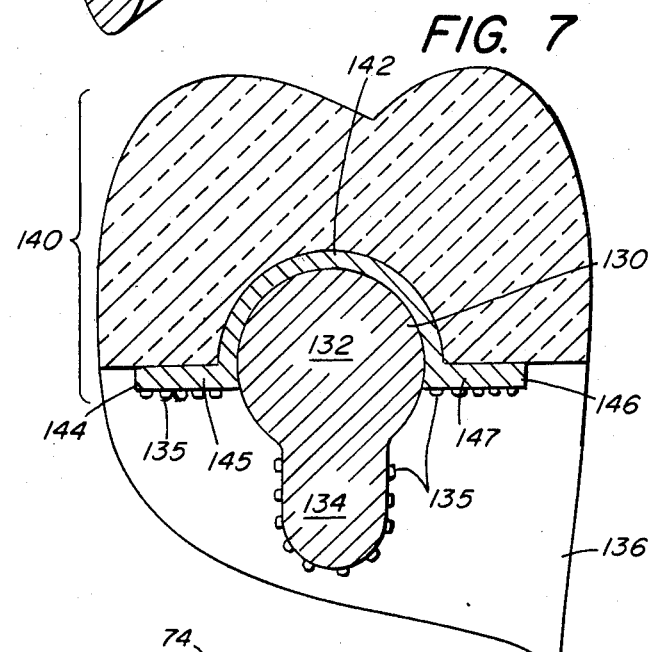
FIG. 7 is a cross-sectional view of another embodiment of the invention.
Figure 8:
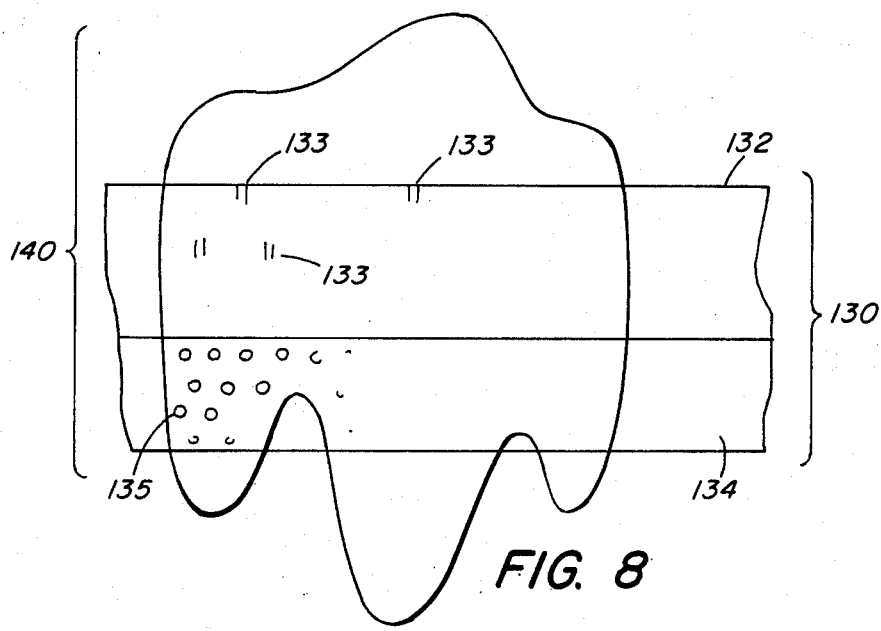
FIG. 8 is a facial-view of FIG. 7.
Figure 21A:
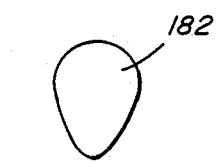
FIGS. 20-24, inclusive, illustrate an additional beam-fixation system according to the invention.
Figure 21B:
Figure 20:
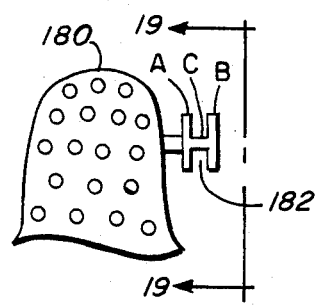

FIG. 7 illustrates another embodiment of the invention, in which a pontic upper part 140 is adjustable in place around a beam, which is not provided with either a groove or a keyway. The beam 130 has a generally round cross-section, the upper portion 132 of which (as viewed in the figure) has a cylindrical cross-section, and the lower portion 134 of which is narrower and rounded on a smaller radius. A pontic upper portion 140, here indicated as a posterior tooth, has a substructure 142 which, in cross-section, appears to drape over the upper part 132 of the beam, with its lower long edges 144, 146 extending laterally outward, on flanges 145, 147, respectively above the lower portion 134. The lower portion 134 of the beam, and the tissue-facing lower surfaces of the flanges 145, 147, are fitted with retentive beads or the like 135, for cosmetic dental reconstruction material 136. As seen in FIG. 8, the beam 130 has grooves 133 circumferentially oriented over the surface of the upper portion 132, for receiving a cement to lock the substructure 142 in place once its orientation around, and position along the beam 130 have been determined. This allows the dentist to rotate the pontic elements into the proper occlusal plane.

Figure 10:
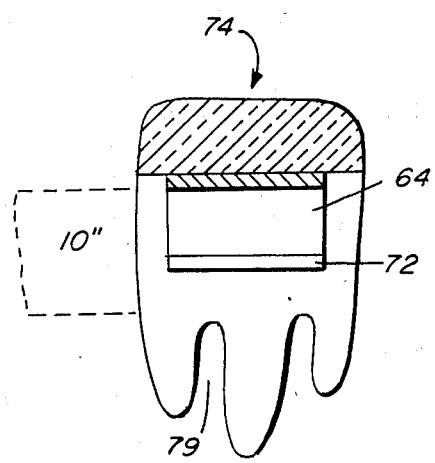
FIG. 10 is a lingual view, partly in section, of FIG. 9.
Figure 9:
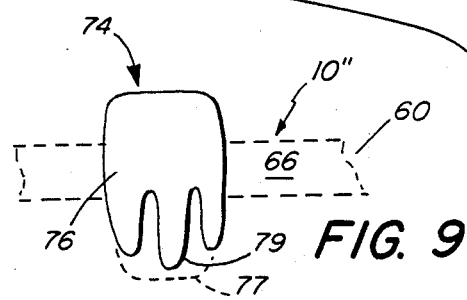
FIG. 9 is a facial view of an upper pontic part for an anterior tooth.

FIGS. 9 and 10 show the facial and lingual aspects of an anterior pontic element, such as the pontic element described above with reference to FIG. 4. The lower edge of the facial aspect 76 of the superstructure 74 ends in a lobular edge 79. When cosmetic material 77 is applied to fasion the lower (i.e.: gingival) pontic part, the boundary between the two parts can be blended along th developmental lobes without showing a visible line between the upper and lower parts of teh pontic. As can be seen in FIG. 10, the substructure 64 extends along the beam 10" nearly the entire distance of the width of the pontic.

Figure 11:
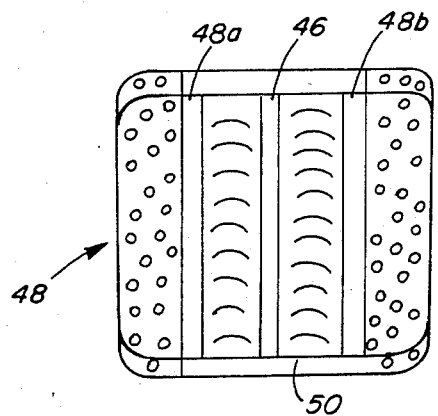
FIG. 11 is a bottom view of the pontic upper portion shown in FIG. 3.

FIG. 11 shows a bottom view of the upper (e.g.: molar) pontic portion 42 of FIG. 3. As in FIG. 10, here, too, the substructure 48 extends a major portion of the length of the superstructure 50 lengthwise of the beam 10'.

Figure 12:
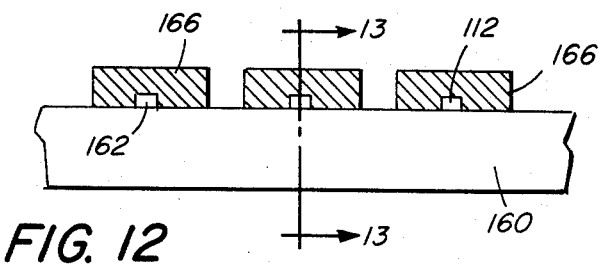
FIGS. 12-14, inclusive, illustrate another embodiment of the beam-pontic support system of the invention.
Figure 13:
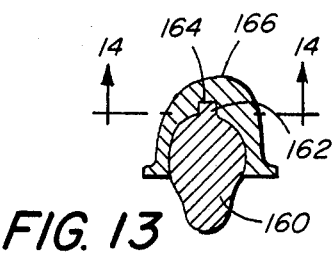
Figure 14:
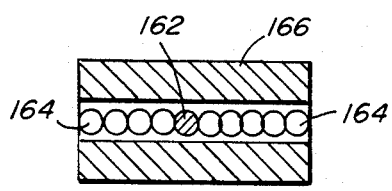

Referring to FIGS. 12-14, inclusive, a beam 160 has a row of studs 162 extending from its upper surface, for coacting with locating apertures 164 in the under-sides of respective substructures 166 for pontic upper portions. As seen in FIG. 14, each substructure 166 has a series of locating apertures in a line running parallel to the long dimension of the beam for fixing the substructure lengthwise of the beam by locating the pin 162 in a selected one of the apertrues. Each pin 162 fixes the corresponding substructure 166 in position along the beam, and around the longitudinal axis of the beam.

Figure 15:
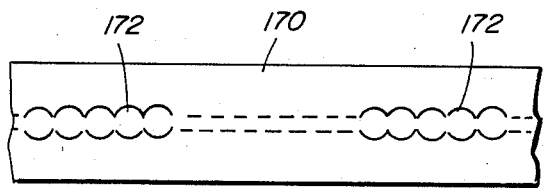
FIGS. 15-17, inclusive, illustrate a variation of the embodiment shown in FIGS. 12-14, inclusive.
Figure 16:
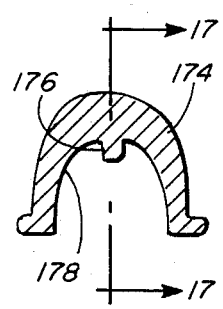
Figure 17:
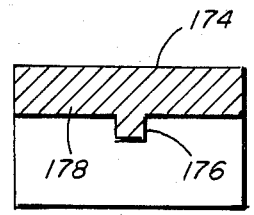

Referring to FIGS. 15-17, inclusive, the arrangement shown is similar to that shown in FIGS. 12-14, inclusive with locating parts reversed. Thus, the beam 170 has a continuous row of locating apertures 172 running in a line along one surface, here an upper surface of the beam, parallel to the longitudinal axis of the beam, and each pontic upper portion substructure 174 has a locating pin 176 in its undersurface which rests on the beam, for locating the substructure along the beam and fixing it against rotation around the beam.

Figure 18:
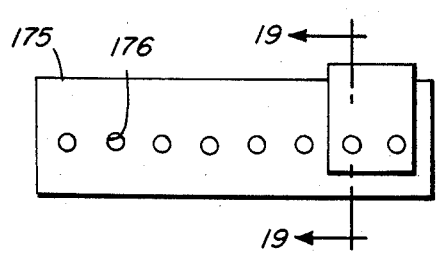
FIGS. 18 and 19 illustrate another embodiment of the beam-pontic support system of the invention;.
Figure 19:
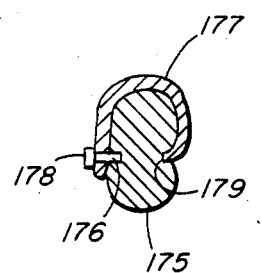

FIGS. 18 and 19 show a still further way to fix a pontic upper portion to a beam. The beam 175 has a row of locating holes 176 in a line along the beam. The substructure 177 (which may be similar to that shown in FIG. 4) has a locating pin or screw on the side opposite to groove 179.

Figure 22:
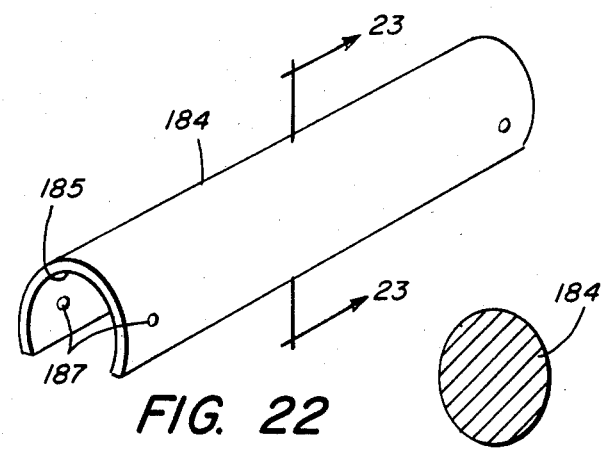
Figure 23:
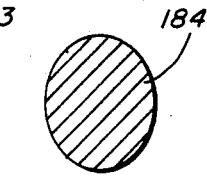
Figure 24:
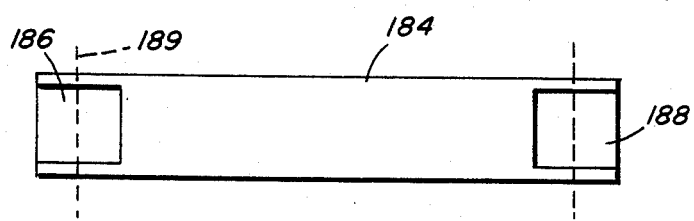

Referring to FIGS. 20 to 25, inclusive, the abutment 180 (exemplary of the abutments 12, 14 in FIGS. 1 and 2) has a mounting stud 182 for a beam 184 which allows a limited amount of adjustment of the beam around its longitudinal axis, before fixing the beam in place; this arrangment provides an additional modality for making occlusal adjustments at chairside. The stud 182 has two transverse plates A and B held spaced-apart by generally central bar C. As seen in FIGS. 21A and B, the plates 182A and B are generally tear-drop shaped, and may be oriented as desired pointed end up, or rounded end up, as viewed in the drawings. The beam 184 has ends 186, 188 which are partly open on the side and fully open end wise, so that they may be fitted over respective studs like the stud 182. The beam 184 is otherwise closed all around and may be solid in cross-section as shown in FIG. 23. The shape of the open ends, as illustrated in FIG. 22, allows the beam to be fitted over a stud 182 oriented as shown in FIG. 21A, so that the inner rounded surface 185 will lie smoothly on the upper rounded surfaces of the plates 182A and 182B. A bolt, rivet, or the like (not shown) can then be passed through holes 187, as is indicated by the dashed line 189 in FIG. 24, and between the plates 182A and B, for tightening the beam 184 on the stud 182, in a desired orientation around the beam axis.

Figure 25:
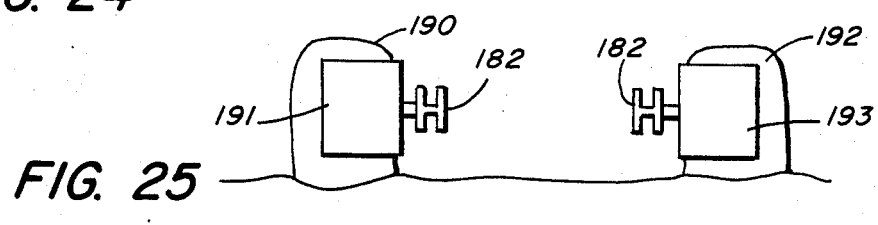
FIG. 25 illustrates attachments affixed via structures adapted to relatively intact abutment teeth.

FIG. 25 shown studs 182, for example, used as attachments fixed to respective relatively intact abutment teeth 190, 192 via structures 191, 193, respectively, which are non-invasively affixed by adhesive means to the teeth. A beam and pontic can be fitted to these attachments as described above.

The components of this new modular system can be made of a wide variety of materials. The beams, substructures and attachments can be made of currently-preferred metals, such as titanium. Alternatively, the beams, substructures and attachments can be made of combustible plastic materials and after being fitted to the patient they can be invested and cast to provide a single rigid structure for supporting one or more pontic upper portions, with all the rigidity and permanence of more expensive fixed-bridges that are made from impressions taken on the patient, but without the time-consuming procedures that are required to make them, and without the frustrating occlusal adjustments that are frequently required after fabrication and installation to make them fit properly. It is presently preferred that the beam, no matter how attached to abutments, will be finally fixed in place with bolts, pins, rivets, screws, attachments or equivalent solid mechanical connection. Beams can be adjustable in length, as by telescoping in design.

I claim:

1. A dental bridge for supporting a pontic having a groove that is open to its gingival aspect, said bridge comprising a substantially flexure-resistant elongated beam, means for fixing said beam disposed generally horizontally between two abutments as a carrying bar for said pontic, said beam having a distributed support surface smoothly-contoured in cross-section, said pontic upper portion having a contact surface in said groove contoured to mate with said support surface, said beam surface being oriented toward said contact surface of said pontic when the latter is present on said beam with said beam in said groove with the latter open toward the gingiva for supporting said pontic against occlusal and/or incisal force on said contact surface while distributing said force substantially uniformly over said beam surface, and means on a lower portion of said beam to retain a locally-applied dental restorative material for filling said groove and completing the lower gingival aspect of said pontic.

2. A dental bridge according to claim 1 including a pontic upper portion fixed on said upper portion of said beam, and a locally-applied dental restorative material fixed to said lower portion of said beam for completing the lower portion of said pontic.

3. A dental bridge according to claim 1 including longitudinally-extending groove means in said beam, said pontic upper portion including means to engage in said groove means for holding said upper portion fixed to said beam against contact-derived forces of displacement around said beam.

4. A dental bridge according to claim 3 wherein said groove means is shaped as a keyway, and said means to engage in said groove means is shaped as a key for mating in said keyway when said key is inserted form an end into said groove means.

5. In a dental bridge according to claim 3 a prefabricated pontic upper portion comprising a pontic substructure for engaging said beam, said substructure including said means to engage in said groove, and a superstructure which includes dental contact surface means fixed to said substructure.

6. A dental bridge for a pontic, comprising a substantially flexure-resistant beam, means for fixing said beam disposed generally horizontally between two abutments as as carrying bar for a pontic, length-wise and width-wise distributed surface means on said beam to support in substantially fixed retention a pontic upper portion having a length-wise and width-wise distributed contact surface contoured to mate with said support means, said support means including a gradually-curved portion of the beam surface which is oriented toward said contact surface of said pontic when the latter is present, for supporting said pontic against occlusal and/or incisal force on said contact surface while distributing said force substantially uniformly over said distributed beam surface, wherein said beam is approximately heart-shaped in cross-section, the lobes of which provide a rounded upper portion of said beam, and means on said beam including said lobes and a reentrant groove between them to support said pontic upper portion against contact-derived forces tending to displace said pontic around said beam, and means on a lower portion of said beam to retain a locally-applied dental restorative material for completing the lower gingival-aspect of said pontic.

7. A dental bridge for a pontic, comprising a substantially flexure-resistant beam, means for fixing said beam disposed generally horizontally between two abutments as a carrying bar for a pontic, length-wise and width-wise distributed surface means on said beam to support in substantially fixed retention a pontic upper portion having a length-wise and width-wise distributed contact surface contoured to mate with said support means, said support means including a gradually-curved portion of the beam surface which is oriented toward said contact surface of said pontic when the latter is present, for supporting said pontic against occlusal and/or incisal force on said contact surface while distributing said force substantially uniformly over said distributed beam surface, wherein said beam is of generally oval-shaped cross-section, and means on a side of said beam intermediate said upper and lower portions thereof to restrain said pontic upper portion against contact-derived forces of displacement around said beam, and means on a lower portion of said beam to retain a locally-applied dental restorative material for completing the lower gingival-aspect of said pontic.

8. Method of fabricating a dental restorative bridge from modular components including a bar and a pontic upper portion comprised of a substructure shaped to embrace said bar and a superstructure fitted to said substructure which provides tooth-shaping surfaces, said bar and said substructure each being made of a combustible material, comprising the steps of:
 (a) temporarily fitting said bar to the patient in the eventually desired position between two abutments supporting said bar;
 (b) locating said pontic upper portion on said bar and making occlusal adjustments at chairside;
 (c) temporarily fixing said substructure to said bar so as to preserve said adjustments;
 (d) separating said superstructure from said substructure;
 (e) investing said bar and said substucture as a unit; and
 (f) casting a single rigid structure which replicates said unit.

9. A method according to claim 8 further including:
 (h) re-fitting said superstucture to said substructure portion of said single rigid structure; and
 (i) fitting a soft-tissue oriented portion of said pontic to the gingival aspects of said bar and said pontic upper portion.

* * * * *